United States Patent [19]

Reger et al.

[11] 4,065,466

[45] Dec. 27, 1977

[54] INTEGRATED PROCESS FOR THE PREPARATION OF 2-DIALKOXYPHOSPHINYLIMINO-1,3-DITHIETANE

[75] Inventors: David William Reger, Trenton; Murray Garber; Don Wesley Long, both of Lawrenceville, all of N.J.

[73] Assignee: American Cyanamid Company, Stamford, Conn.

[21] Appl. No.: 695,667

[22] Filed: June 14, 1976

[51] Int. Cl.$^2$ .......................................... C07D 339/00
[52] U.S. Cl. ................................ 260/327 M; 260/947
[58] Field of Search .................................. 260/327 M

[56] References Cited

U.S. PATENT DOCUMENTS 3,470,207    9/1969    Addor .................................. 260/327

*Primary Examiner*—Cecilia M. S. Jaisle
*Attorney, Agent, or Firm*—Harry H. Kline

[57] ABSTRACT

There is provided a fully integrated process for preparing a 2-dialkoxyphosphinylimino-1,3-dithietane in good overall yields with considerable savings in materials, time and labor involving a plurality of steps comprising the overall reaction of a dialkoxyphosphoryl chloride and an alkali metal or ammonium thiocyanate to obtain a dialkoxyphosphinyl isothiocyanate, reacting the latter with 1.1 to 1.2 molar equivalents of an alkali mercaptan in the presence of a water and, finally, reacting resultant dialkoxyphosphinyldithiocarbamate with methylene bromide or methylene iodide in the presence or absence of a non-ionic surfactant under controlled pH conditions ranging from 5 to 8 to obtain resultant 2-dialkoxyphosphinylimino-1,3-dithietane. The latter finds utility for the control of root-knot nematode.

11 Claims, No Drawings

INTEGRATED PROCESS FOR THE PREPARATION OF 2-DIALKOXYPHOSPHINYLIMINO-1,3-DITHIETANE

SUMMARY OF THE INVENTION

The broad spectrum contact and systemic pesticide 2-diethoxyphosphinylimino-1,3-dithietane represented by the formula below:

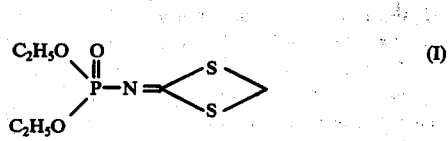

and a method of preparation thereof have been disclosed and claimed in U.S. Pat. No. 3,470,207 issued, Sept. 30, 1969, and a method of use thereof has been disclosed and claimed in U.S. Pat. No. 3,553,319 issued, Jan. 5, 1971. Further, the intermediate product, diethoxyphosphinyldithiocarbamate, and a method of preparation thereof have been disclosed and claimed in U.S. Pat. No. 3,476,837 issued, Nov. 4, 1969. Each of the above referred-to U.S. patents is incorporated herein by way of reference.

The aforementioned pesticide has been found to be quite effective for the control of soil dwelling nematodes and especially for the control of root-knot nematodes (*Meloidogyne incognita*). Thus, it is of substantial importance to be able to manufacture 2-diethoxyphosphinylimino-1,3-dithietane economically on a large scale.

Unfortunately, the preparation of 2-diethoxyphosphinylimino-1,3-dithietane by methods known in the art, while satisfactory for small scale production, is not suitable for large scale preparations of said compound. For illustrative purposes, one such prior art process consisting of three (3) distinct and separate steps is hereinbelow briefly described employing diethoxyphosphoryl chloride as the illustrative starting reactant.

Step 1

One molar equivalent of diethoxyphosphoryl chloride is reacted with a 1.1 to 1.2 molar equivalent of anhydrous ammonium thiocyanate in the presence of an insert solvent, such as benzene, toluene, xylene or the like, at about 20° C to 30° C. The thus-obtained solution of diethoxyphosphinyl isothiocyanante is washed several times with water and dilute sodium bicarbonate solution, and then the isothiocyanate is isolated by removing the solvent in vacuo. This reaction (Step 1) may be graphically illustrated as follows:

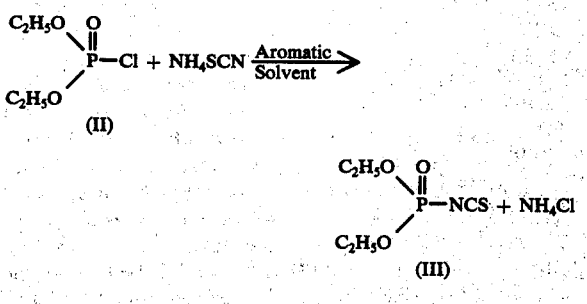

Step 2

Diethoxyphosphinyl isothiocyanate obtained in Step 1 above, is reacted with from 1.1 to 1.2 molar equivalents of sodium hydrosulfide or potassium hydrosulfide, freshly prepared in situ, prior to the addition of said isothiocyanate, from hydrogen sulfide and sodium or potassium hydroxide or alkoxide (e.g. t-butoxide) in a lower ($C_1$–$C_3$) alcohol, to yield the corresponding alkali metal diethoxyphosphinyldithiocarbamate. This reaction is quite rapid and is complete in a relatively short time. The thus-obtained dithiocarbamate of formula (IV) may be isolated if desired, but the isolation procedure is cumbersome, and since the dithiocarbamate is relatively unstable, it is more convenient to use the above reaction mixture in the following final step.

This reaction (Step 2) may be graphically illustrated as follows:

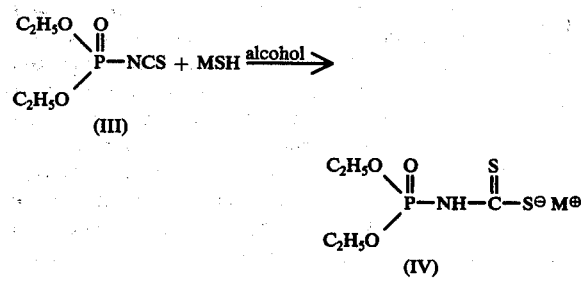

where M is sodium or potassium.

Step 3

To the Step 2 reaction mixture there are added from 2.5 to 10 molar equivalents of methylene bromide, bromochloromethane, or methylene iodide in the presence of an acid acceptor, such as sodium bicarbonate. The reaction mixture is then stirred at room temperature for at least 8 hours to yield 2-diethoxyphosphinylimino-1,3-dithietane of formula (I). The product dithietane is isolated from the reaction mixture by standard laboratory procedures and purified, if necessary. This reaction step may be graphically illustrated as follows:

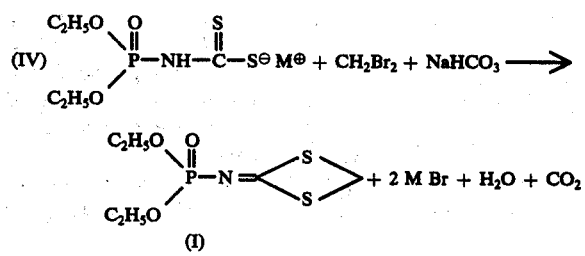

where M is sodium or potassium.

As hereinabove stated, this and similar processes of the prior art, while suitable for small scale preparations of 2-diethoxyphosphinylimino-1,3-dithietane, are not suitable for its manufacture on a large scale. The required washing of formula (III) intermediate with water and aqueous sodium bicarbonate to remove impurities can cause exothermic decomposition of said intermediate. In addition, the use of solvents, the relatively long reaction times required, and the need for the purification of the intermediates in general, coupled with the inevitable losses suffered during the work-up and purification of the intermediates and of the end product, make this and similar approaches economically undesirable.

Surprisingly, it has been found that the desired 2-diethoxyphosphinylimino-1,3-dithietane of formula (I) above may be conveniently prepared on a large scale, in satisfactory overall yields, by the novel fully integrated process of the present invention. The term "fully integrated process" is used herein to indicate that in this process the hereinabove described individual reaction steps leading to the desired formula (I) dithietane are combined into one continuous and interlocking sequence of reactions, whereby the need to isolate and/or purify said intermediates is eliminated. The reaction mixtures containing said intermediates and any by-products and impurities formed in the reaction are employed as such in each subsequent step of the process.

In general, it is advantageous to carry out the hereinabove described Step 3 of the prior practice in water, thereby eliminating the time and cost associated with recovery and recycle of an organic solvent. To accomplish this desired result, it is critical to control the pH within well defined pH limits to minimize decomposition of the intermediates and other products. Moreover, it has been found that the use of a nonionic surfactant, such as ethylene oxide condensates, polyoxyethylene condensates, polyoxyethylenepolyoxypropylene condensates and the like increases the yield of the hereinabove defined Step 3 reaction.

In addition to the above, it has been found that, by integrated process of the present invention the reaction times of each of the interlocking steps are shortened without adverse effect on the yields, and the product, a 2-dialkoxyphosphinylimino-1,3-dithietane, is obtained in satisfactory overall yields usually ranging from 60% to 75%.

The fully integrated process of the present invention is hereinbelow described and graphically illustrated in a detailed manner utilizing as illustrative diethoxyphosphoryl chloride as the starting reactant.

Step 1

One molar equivalent of diethoxyphosphoryl chloride of formula (II) is reacted with 1.0 to 1.2 molar equivalent of sodium-, potassium- or ammonium thiocyanate at a temperature range of 5° C to 30° C and, preferably, 15° C to 25° C for a period of time ranging from 2 to 4 hours to yield diethoxyphosphinyl isothiocyanate of formula (III). The reaction is slightly exothermic, but is easily controlled by a cooling bath.

The above reaction mixture containing the isothiocyanate of formula (III) is used without isolation or delay in the following step.

Step 2

The reaction mixture of Step 1, containing the isothiocyanate of formula (III) is added slowly to an aqueous solution of a 1.1 to 1.2 molar equivalent of sodium-, potassium or ammonium hydrosulfide at a temperature range of 5° C to 30° C and, preferably, 15° C to 25° C. The reaction is exothermic, but is easily controlled with a cooling bath. The reaction is rapid and is complete in about 10 to 15 minutes after the addition of the Step 1 reaction mixture is completed. The reaction of Step 2 containing diethoxyphosphinyldithiocarbamate of formula (IV) is utilized in the final step of the process.

Step 3

A 1.0 to 2.0 molar equivalent and preferably 1.0 to 1.3 molar equivalent of a methylene halide, such as methylene bromide and methylene iodide, is added to the Step 2 aqueous reaction medium containing sodium (potassium or ammonium)-diethoxyphosphinyldithiocarbamate of formula (IV). If desired, a nonionic surfactant, such as ethylene oxide condensates, polyoxyethylene condensates, polyoxyethylenepolyoxypropylene condensates and the like, may be added to the latter reaction mixture in amounts ranging from about 0.1% to 5.0%, by weight, and, preferably, 0.5% to 1.5%, by weight, of said reaction mixture. The temperature of the two phase mixture is adjusted to about 25° C to 45° C and, preferably, 28° C to 40° C. The reaction mixture is stirred at the above temperature and as the reaction commences, the pH of the reaction mixture is lowered, due to halo acid formation (HBr or HI) in the reaction mixture. Aqueous ammonium hydroxide or other suitable base, such as sodium hydroxide, potassium, hydroxide, sodium or potassium carbonate and the like, is added, as needed, to maintain a pH range between 5 and 8 and, preferably, from 6 to 7, to minimize losses due to decomposition of the intermediates and/or product. Under the conditions set forth above, the reaction is complete in about 2 to 5 hours, and the resultant 2-diethoxyphosphinylimino-1,3-dithietane is present in an aqueous medium, since the organic phase comprising the methylene halide reactant is consumed during reaction. The thus obtained produce of formula (I) is extracted from the aqueous reaction mixture with a suitable solvent and recovered from the solution, if desired, by removing the solvent. The above described reaction sequence may be graphically illustrated as follows:

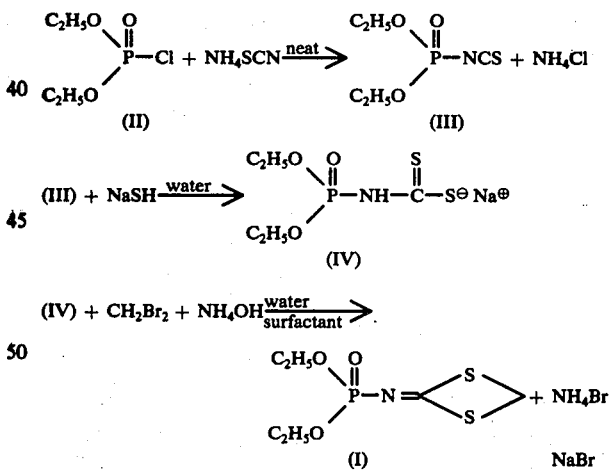

It is of advantage to introduce an inert organic solvent, such as benzene, toluene, xylene, ethylene dichloride, chloroform, methylene chloride and methylene bromide, in Step 1 of the above described fully integrated process. This seemingly minor change in said process is quite significant and of great advantage of a production scale. First, the above-identified thiocyanates are quite hygroscopic and thus tend to absorb moisture from the air while being charged to the reactor containing the diethoxyphosphoryl chloride reactant, and thus normally would require protective blanketing with an inert gas such as nitrogen. This involves the use of special equipment to load the reactor, since the presence of even small amounts of water significantly reduce the overall yields of said process. The use of one of the above-identified solvents allows the rapid introduction of the thiocyanate into the reactor with minimum exposure to air and the moisture contained therein, and, thereafter, said solvent serves as a protective liquid blanket preventing said thiocyanate from absorbing moisture from the air and thus eliminates the need to use special equipment and an inert gas during the addition of said thiocyanate. Advantageously, this change allows the addition of diethoxyphosphoryl chloride (a toxic liquid) in a closed system to the stirred slurry of anhydrous thiocyanate in said solvent, and since the ensuing reaction is exothermic, the exotherm is easily controlled by adjusting the rate of addition of said phosphoryl chloride accordingly. Further, said solvent serves as an inert diluent and thus allows a more thorough stirring, mixing and pumping of an otherwise thick reaction mixture. Thus, there is no need to employ special, high powered stirring and pumping equipment and, therefore, additional savings in energy requirements can be realized. The presence of said solvent in Step 2 does not adversely effect the yields of this step, and since it is separated from the aqueous phase of the Step 2 reaction mixture when said reaction step is completed, it aids in the removal of solvent soluble impurities which may be present in said mixture.

In a preferred embodiment, the process of the present invention encompasses the following detailed steps:

To a stirred slurry of 1.0 to 1.1 molar equivalent of anhydrous sodium, potassium or ammonium thiocyanate in about 50 ml to 100 ml of a solvent such as benzene, toluene, xylene, ehtylene dichloride, chloroform, methylene chloride or methylene bromide, is added one molar equivalent of diethoxyphosphoryl chloride of formula (II) at a temperature range of 5° C to 30° C and, preferably, 15° C to 25° C and the reaction mixture stirred for a period of time from 4 to 4 hours to yield diethoxyphosphinyl isothiocyanate of formula (III). The reaction is slightly exothermic and such exotherm easily is controlled by either adjusting the rate of addition of said phosphoryl chloride or by using a cooling bath, or by a combination of the two.

The above mixture, containing the diethoxyphosphinyl isothiocyanate, is then added slowly to an aqueous solution of 1.1 to 1.2 molar equivalent of sodium, potassium or ammonium hydrosulfide at a temperature range of 5° C to 35° C and, preferably, 25° C to 30° C. The ensuing reaction is quite rapid and is complete in about 10 to 15 minutes after the addition of the reaction mixture (from Step 1) is completed. Next, the solvent phase of the thus obtained two phases reaction mixture is separated from the aqueous phase, and is discarded or recovered for reuse. The aqueous phase, containing the diethoxyphosphinyldithiocarbamate, is utilized in the final step as follows:

A 1.0 to 2.0 molar equivalent and, preferably, a 1.0 to 1.3 molar equivalent of a methylene halide such as methylene bromide and methylene iodide is mixed with an equal volume of water and a nonionic surfactant as for instance ethylene oxide condensates, polyoxyethylene condensates, and polyoxyethylene-polyoxypropylene condensates and commercially available under the tradename Pluronic manufactured by Wyandotte - BASF, is added in amounts ranging from about 0.1% to 5.0%, by weight, and preferably, 0.5% to 1.5%, by weight, of the reaction mixture. The temperature of the stirred two phase mixture is adjusted to about 25° C to 45° C and, preferably, 30° C to 35° C. Immediately, thereafter, 25% by volume of the aqueous solution of the dithiocarbamate of formula (IV) obtained in the above reaction step is added to said mixture. As the reaction commences, the pH of the reaction mixture slowly decreases and when it reaches the range of pH 5 to 8 and preferably pH 6 to 7, an aqueous solution of a base, selected from ammonium hydroxide, sodium or potassium hydroxide, sodium or potassium carbonate and the like, is added at a rate to maintain the pH of said reaction in the specified range.

Thereafter, the remaining dithiocarbamate solution is added at a controlled rate so as to maintain a steady consumption of base with cooling as needed to keep the temperature in the range of 25° C to 45° C and preferably 30° C to 35° C. Additional amounts of base are added, as needed, to maintain the pH of the reaction in the specified range until the reaction is complete. The reaction time is 2 to 6 hours and usually 3 to 5 hours.

On completion of the reaction, the mixture is cooled and the organic phase separated. The aqueous phase is backwashed with a solvent, selected from the group of solvents named above. The organic phase and the solvent wash are combined, approximately an equal volume of water is added and the pH of the resultant two phase mixture adjusted to 8 and the mixture stirred for about 30 minutes. The organic phase is then separated. The aqueous is backwashed with a solvent as above, and the washings are combined with the organic phase. The product of formula (I) is recovered by removing said organic phase in vacuo.

In the thus described integrated process overall yields of 65% to 75% of theory are realized.

Substitution of bromochloromethane for methylene bromide (or iodide) in the above integrated process results in significantly reduced yields of 2-diethoxyphosphinylimino-1,3-dithietane.

Advantageously, analogs of formula (I) 2-diethoxyphosphinylimino-1,3-diethietane represented by formula:

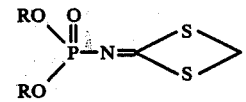

wherein R is selected from the group consisting of methyl, isopropyl, n-butyl, and isomers thereof; can be prepared by the novel process of the present invention.

The desired 2-diethoxyphosphinylimino-1,3-dithietane nematocide may be formulated for use by accepted methods, as liquid or emulsifiable concentrates, wettable powders, dusts, dust concentrates and granular formulations.

The following non-limiting examples are incorporated herein to further illustrate the present invention.

EXAMPLE 1

Dry ammonium thiocyanate (67.0 g; 0.88 mole) is added over a 10 minute period at 5° C with stirring to diethoxyphosphoryl chloride (138.0 g;0.80 mole). The ensuing reaction is exothermic and the temperature of the reaction mixture is maintained below 25° C with an ice bath. The resulting slurry is allowed to warm to 25° C and stirred 4 hours. The slurry is then cooled to 5° C and washed 3 minutes with cold water (170 ml), the aqueous phase separated and discarded.

The diethoxyphosphinyl isothiocyanate obtained in the above step is added slowly to a solution of sodium hydrosulfide monohydrate (74.0 g – 73% real; 1.0 mole) in water (200 ml) at 5° C. The ensuing reaction is also exothermic and the temperature of the reaction is maintained below 25° C by controlling the rate of addition of the isothiocyanate. The resulting slurry of sodium diethoxyphosphinyldithiocarbamate is stirred an additional 10 minutes at 15° C to 20° C after the addition of the isothiocyanate is completed.

A Pluronic L-62 nonionic polyoxyethylene-polyoxypropylene surfactant (3.0g) is added to the dithiocarbamate slurry and the pH of the system adjusted from 7.7 to 6.0 with concentrated hydrochloric acid (8.5 ml). Methylene bromide (139.1 g; 0.80 mole) is then added to the slurry. The reaction mixture is stirred at 25° C to 27° C and ammonium hydroxide solution (15%) added as needed to maintain the pH at 6.0. The reaction is run for 4-¾ hours and a total of 107 ml of 15% ammonium hydroxide is added.

The organic phase is separated, the aqueous phase washed with toluene (2×50ml) and the toluene washings are combined with the organic phase. The combined organic phase is washed with saturated aqueous sodium bicarbonate solution (3×100 ml). The combined sodium bicarbonate solutions are backwashed with toluene (50 ml) and the toluene layer added to the above organic phase. The organic phase is evaporated to constant weight to afford 139.3 g (86.4% real; 62.3% yield) of title product.

Substitution of dimethoxyphosphoryl chloride, di-n-propoxyphosphoryl chloride, diisopropoxyphosphoryl chloride di-n-butoxyphosphoryl chloride and di-tert-butoxyphosphoryl chloride for diethoxyphosphoryl chloride in the process of Example 1 above affords 2-dimethoxyphosphinylimino-1,3-dithietane, 2-di-n-propoxyphosphinylimino-1,3-dithietane, 2-di-isopropoxyphosphinylimino-1,3-dithietane, 2-di-n-butoxyphosphinylimino-1,3-dithietane, and 2-di-tert-butoxyphosphinyl imino-1,3-dithietane, respectively.

EXAMPLE 2

To a stirred slurry of dry sodium thiocyanate (68.1 g; 0.84 mole) in toluene (64 ml) at 20° C diethoxyphosphoryl chloride (138 g; 0.80 mole) is added. After the addition is completed the reaction mixture is stirred at 25° C for 3 hours.

The diethoxyphosphinyl isothiocyanate obtained above is added over 1 hour to a solution of sodium hydrosulfide monohydrate (74 g – 73% real; 1.0 mole) in water (200 ml). The ensuing reaction is exothermic. The temperature of the reaction mixture is maintained between 20° C and 30° C. After the addition is completed, the temperature is adjusted to 30° C, the two phase mixture is separated and the toluene phase discarded.

Water (72 ml), methylene bromide (180.8 g; 1.04 mole) and 3 g of Pluronic L-62 which is a polyoxyethylene-polyoxypropylene condensate (manufactured by Wyandotte-BASF) are charged into a reaction vessel. The temperature of the mixture is adjusted to 35° C and 25% of the aqueous dithiocarbamate solution obtained in the above step is added to the mixture. The pH of the reaction mixture drops to 6.5 during a 1 hour period. Concentrated ammonium hydroxide is added to maintain the pH between 6 to 7. The reaction is run by periodically adding 15% to 20% of the aqueous dithiocarbamate solution to the reaction mixture, followed by the addition of concentrated ammonium hydroxide to maintain the pH between 6 and 7. The reaction time is 3 hours and 10 minutes.

The reaction mixture is then cooled to 25° C and the organic phase separated. The aqueous phase is backwashed with toluene (200 ml) and then discarded. The above organic phase and the toluene wash are recycled to the reaction vessel. Water (250 ml) is added, the pH of the two phase system adjusted to 8 with ammonium hydroxide solution, and the mixture stirred for 30 minutes. The organic phase is then separated. The aqueous phase is backwashed with toluene (160 ml). The organic phase and the toluene wash are combined and stripped to constant weight in vacuo to afford 163.3 g (89% real; 75% yield) of title product.

EXAMPLES 3 –8

The following illustrate the effect of pH changes in Step 3 on the yields of 2-diethoxyphosphinylimino-1,3-dithietane without the use of surfactant.

The process of Example 1 is repeated in every detail except that no surfactant is included in Step 3 of the process, and that the solvent is an acetone:water mixture (1:10). Variables are tabulated below, with the results obtained.

TABLE I

| Example | acetone:water ratio in ml | pH of Step 3 | % Yield of Product |
|---|---|---|---|
| 3 | 20:200 | 5 | 47.9 |
| 4 | 20:200 | 6 | 59.8 |
| 5 | 0:200 | 6 | 57.7 |
| 6 | 20:200 | 7 | 53.7 |
| 7 | 20:200 | 8 | 41.58 |
| 8 | 20:200 | 10 | <10 |

It can be clearly seen from the above table that optimal yields are obtained in the range of pH 6 to 7.

EXAMPLE 9

The following illustrates the preparation of 2-diethoxyphosphinylimino-1,3-dithietane by a fully integrated process without any surfactant.

To a stirred slurry of dry sodium thiocyanates (68.1 g; 0.84 mole) in toluene (64 ml) at 20° C diethoxyphosphoryl chloride (138 g; 0.8 mole) is added over 1 hour. After the addition is completed, the reaction mixture is stirred at 25° C. for 2.5 hours.

The diethoxyphosphinyl isothiocyanate obtained above is added over 1 hour to a solution of sodium hydrosulfide monohydrate (74.0 g – 73% real; 1.0 mole) in water (200 ml) at 15° C to 25° C. The ensuing reaction is exothermic. The temperature of the reaction mixture is maintained between 15° C and 25° C. After the addition is completed, the temperature is adjusted to 30° C, the two phase mixture is separated and the toluene phase discarded.

Water (72 ml) and methylene bromide (180.8 g; 1.04 mole) are charged into a reaction vessel. The temperature of the mixture is adjusted to 35° C and 25% of the aqueous dithiocarbamate solution obtained in the above step is added to the mixture. The pH of the mixture drops to 6.5 during a 1 hour period. Concentrated ammonium hydroxide is added to maintain the pH between 6 and 7. The reaction is run by periodically adding 15% to 20% of the aqueous dithiocarbamate solution to the reaction mixture, followed by the addition of concentrated ammonium hydroxide to maintain the pH between 6 and 7. On completion of the reaction, the reaction mixture is cooled to 25° C and the organic phase is separated. The aqueous phase is backwashed with toluene (200 ml) and then discarded. The above organic phase and the toluene wash are recycled to the reaction vessel. Water (250 ml) is added, the pH of the two phase system adjusted to 8 with ammonium hydroxide solution, and the mixture is stirred for 30 minutes. The organic phase is then separated and stripped to constant weight in vacuo to afford the desired product in good yield.

EXAMPLE 10

The above Example 9 is repeated in every detail except that the final step (i.e. the condensation of the dithiocarbamate with methylene bromide) is run at 40° C. Good yield of desired product is obtained.

The data obtained in the above Examples 9 and 10 above are summarized in Table II.

TABLE II

| Example | Temp. °C of 3rd Step | Product g. as is | Purity % | Product g. real | Yield % |
|---|---|---|---|---|---|
| 9 | 35 | 146.6 | 85.7 | 125.6 | 65.2 |
| 10 | 40 | 144.2 | 85.8 | 123.7 | 64.1 |

We claim:

1. A process for preparing a compound of the formula:

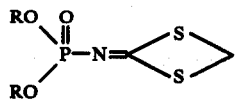

wherein R is alkyl $C_1-C_4$ comprising the steps of: (a) reacting a compound of formula:

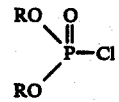

wherein R is as defined above with an anhydrous thiocyanate selected from sodium, potassium and ammonium thiocyanate at a temperature range of 5° C to 30° C to obtain a compound of formula:

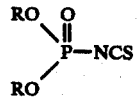

wherein R is as defined above (b) reacting the latter thus-formed compound with a hydrosulfide selected from the group consisting of sodium hydrosulfide, potassium hydrosulfide and ammonium hydrosulfide in an aqueous environment containing a non-ionic surfactant at a temperature range of 5° C to 30° C to obtain a compound of the formula:

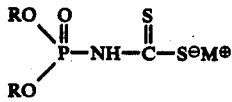

wherein R is as defined above and M is sodium, potassium or ammonium; (c) reacting the thus-formed compound with a methylene halide selected from methylene bromide and methylene iodide in an aqueous environment at a temperature range of 25° C to 45° C and a pH range of 5 to 8, and (d) recovering desired product.

2. The process for preparing the compound of claim 1 having the formula:

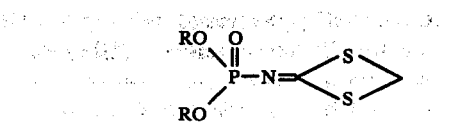

wherein R is alkyl $C_1-C_4$ comprising the steps of: (a) reacting one molar equivalent of a compound of formula:

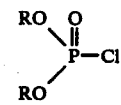

wherein R is as defined above with a 1.0 to 1.1 molar equivalent of an anhydrous thiocyanate selected from the group consisting of sodium thiocyanate, potassium thiocyanate and ammonium thiocyanate at a temperature range of 5° C to 30° C to obtain a compound of formula:

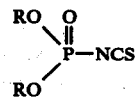

wherein R is as defined above, (b) reacting the thus-formed compound without isolation from the above reaction mixture, in an aqueous environment containing a non-ionic surfactant with 1.1 to 1.2 molar equivalent of a hydrosulfide selected from the group consisting of sodium hydrosulfide, potassium hydrosulfide and ammonium hydrosulfide at a temperature range of 5° C to 30° C to obtain a compound of formula:

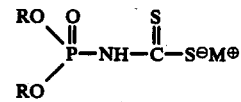

wherein R is as defined above and M is sodium, potassium or ammonium according to the hydrosulfide selected above; and (c) reacting the thus-formed compound without isolation from the above reaction mixture and in the presence of same, with a 1.0 to 2.0 molar equivalent of a methylene halide selected from the group consisting of methylene bromide and methylene iodide at a temperature range of 25° C to 45° C and a pH range of 5 to 8, for a period of time sufficient to complete the reaction.

3. The process according to claim 2, wherein from about 0.1% to about 5.0%, by weight, of the non-ionic surfactant is selected from the group consisting of ethylene oxide condensates, polyoxyethylene condensates and polyoxyethylene-polyoxypropylene condensates.

4. The process according to claim 3, wherein the thiocyanate is sodium thiocyanate and the temperature of the reaction is 15° C to 25° C; the hydrosulfide is sodium hydrosulfide and the temperature of the reaction is 15° C to 25° C' the surfactant is a polyoxyethylene-polyoxypropylene condensate, the amount of said condensate being 0.5% to 1.5%, by weight, of the reaction mixture; the methylene halide is methylene bromide; the temperature of the reaction is 30° C to 40° C; and the pH range is 6 to 7.

5. The process according to claim 2, wherein R is ethyl.

6. The process according to claim 2, wherein the pH of the reaction mixture following addition of the methylene halide is maintained at a pH between about 6 to 7.

7. The process for the preparation of the compound of claim 1 having the formula:

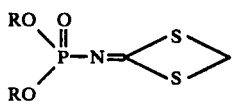

wherein R is alkyl $C_1$-$C_4$ comprising the step of: (a) adding one molar equivalent of a compound of formula:

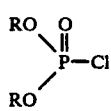

wherein R is as defined above to a slurry of 1.0 to 1.1 molar equivalent of an anhydrous thiocyanate selected from the group consisting of sodium thiocyanate, potassium thiocyanate and ammonium thiocyanate in an anhydrous inert solvent selected from the group consisting of benzene, toluene, xylene, ethylene dichloride, chloroform, methylene chloride and methylene bromide, (b) agitating said resultant mixture at a temperature range of 5° C to 30° C for a period of time sufficient to essentially complete the reaction and obtain a compound of the formula:

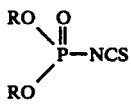

wherein R is as defined above (c) adding the above reaction mixture containing said compound directly to an aqueous solution of a 1.1 to 1.2 molar equivalent of a hydrosulfide selected from the group consisting of sodium hydrosulfide, potassium hydrosulfide and ammonium hydrosulfide, (d) agitating said two phase mixture at a temperature range of 5° C to 30° C for a period of time sufficient to essentially complete the reaction and obtain a compound of formula:

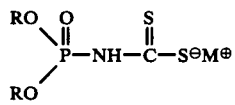

wherein R is as defined above and M is sodium, potassium or ammonium according to the hydrosulfide selected above, (e) separating the aqueous phase of the above two phase reaction mixture containing the above dithiocarbamate compound, (f) adding both said aqueous phase to a methylene halide selected from the group consisting of methylene bromide and methylene iodide present in an aqueous environment and an aqueous solution of a base selected from the group consisting of sodium hydroxide, potassium hydroxide, ammonium hydroxide, sodium carbonate, potassium carbonate, sodium bicarbonate and potassium bicarbonate at a rate so as to maintain the pH of the reaction mixture in the range of 5 to 8 at a temperature range of 25° C to 45° C, for a period of time sufficient to essentially complete the reaction.

8. The process according to claim 7, wherein from 0.1% to 5.0%, by weight, of a nonionic surfactant selected from the group consisting of ethylene oxide condensates, polyoxyethylene condensates, and polyoxyethylene-polyoxypropylene condensates, is added to the aqueous environment containing said methylene halide reactant immediately prior to the addition of the aqueous phase containing said dithiocarbamate reactant and aqueous base as defined above.

9. The process according to claim 8, wherein R is ethyl; the thiocyanate is sodium thiocyanate; the solvent is toluene and the temperature of the reaction is 15° C to 25° C; the hydrosulfide is sodium hydrosulfide and the temperature of the reaction is 15° C to 25° C; the methylene halide is methylene bromide; the nonionic surfactant is a polyoxyethylene-polyoxypropylene condensate, said condensate being present in an amount ranging from 0.5% to 1.5%, by weight, of the reaction mixture; the temperature of the reaction is 30° C to 40° C and the pH range is 6 to 7.

10. A process according to claim 7, wherein R is ethyl.

11. A process according to claim 7, wherein the pH of the aqueous environment following addition of the dithiocarbamate to the methylene halide is maintained at a pH between about 6 and 7.

* * * * *